United States Patent
Qiu et al.

(10) Patent No.: US 10,008,960 B2
(45) Date of Patent: Jun. 26, 2018

(54) ULTRASONIC ACTUATOR DEVICE AND APPLICATIONS THEREOF

(71) Applicant: Max-Planck-Gesellschaft zur Foerderung der Wissenschaften e.V., Munich (DE)

(72) Inventors: Tian Qiu, Stuttgart (DE); Peer Fischer, Freiburg (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 305 days.

(21) Appl. No.: 14/974,410

(22) Filed: Dec. 18, 2015

(65) Prior Publication Data
US 2016/0181951 A1    Jun. 23, 2016

(30) Foreign Application Priority Data
Dec. 23, 2014 (EP) .................................... 14004399

(51) Int. Cl.
*H02N 2/10* (2006.01)
*A61B 17/00* (2006.01)
*F03G 7/00* (2006.01)

(52) U.S. Cl.
CPC ............ *H02N 2/108* (2013.01); *A61B 17/00* (2013.01); *F03G 7/002* (2013.01); *H02N 2/103* (2013.01); *A61B 2017/00398* (2013.01)

(58) Field of Classification Search
CPC .......... A61B 17/00; A61B 2017/00398; F03G 7/002; H02N 2/103; H02N 2/108
See application file for complete search history.

(56) References Cited

U.S. PATENT DOCUMENTS

| 5,523,643 A | 6/1996 | Fujimura et al. |
| 5,770,913 A | 6/1998 | Mizzi |

(Continued)

FOREIGN PATENT DOCUMENTS

| JP | 2009136939 A | 6/2009 |
| JP | 2013183563 A | 9/2013 |

OTHER PUBLICATIONS

Denisov, "Micromechanical Actuators Driven by Ultrasonic Power Transfer", Journal of Microelectromechanical Systems, vol. 23, No. 3, pp. 750-759 (2014).

(Continued)

*Primary Examiner* — Scott T Luan
(74) *Attorney, Agent, or Firm* — Caesar Rivise, PC (57) ABSTRACT

Ultrasonic actuator device (100) includes actuator arm arrangement (10) including first and second actuator sections (11,12), wherein the first section is arranged for coupling with support structure (50) and the second section is movable relative to the first section, and ultrasonic driver device (20) including at least one ultrasonic driver unit (21-28) coupled with at least one of first and second sections for driving actuator arm arrangement (10) and for providing movement of the second section relative to the first section, and wherein actuator arm arrangement (10) is movable with at least two degrees of freedom and the at least one ultrasonic driver unit includes an array of oscillating elements being arranged for creating an acoustic stream in an adjacent medium in response to application of ultrasound. Furthermore, an operational instrument including at least one ultrasonic actuator device (100) and a method of using the device are described.

19 Claims, 6 Drawing Sheets

(56) References Cited

U.S. PATENT DOCUMENTS

| | | |
|---|---|---|
| 5,906,579 A | 5/1999 | Vander Salm et al. |
| 6,272,922 B1 | 8/2001 | Stevens et al. |
| 8,147,403 B2 | 4/2012 | Takahashi et al. |
| 2013/0271088 A1 | 10/2013 | Hwang et al. |

OTHER PUBLICATIONS

Dijkink et al., "The 'acoustic scallop': a bubble-powered actuator", J. Micromech. Microeng., vol. 16, pp. 1653-1659 (2006).

Epstein, "Millimeter-Scale, MEMS Gas Turbine Engines", Proceedings of ASME Turbo Expo, pp. 1-28 (2003).

Faulhaber: Brushless DC-Micromotor 0206, Data Sheet (http://www.u-motor.com.cn/BL-motorF/PDF/0206.pdf), accessed Jan. 21, 2016.

Feng et al., "Micro Propulsion in Liquid by Oscillating Bubbles", MEMS 2013, Taipei, Taiwan, pp. 63-66 (2013).

Feng et al., "Two-Dimensionally Steering Microswimmer Propelled by Oscillating Bubbles", MEMS 2014, San Francisco, CA, pp. 188-191 (2014).

Hashmi et al., "Oscillating bubbles: a versatile tool for lab on a chip applications", Lab Chip, vol. 12, pp. 4216-4227 (2012).

Liu et al., "A brief review of actuation at the micro-scale using electrostatics, electromagnets and piezoelectric ultrasonics", Acoust. Sci. & Tech., vol. 31, No. 2, pp. 115-123 (2010).

Nama et al., "Investigation of acoustic streaming patterns around oscillating sharp edges", Lap Chip, vol. 14, pp. 2824-2836 (2014).

Ovchinnikov et al., "Acoustic streaming of a sharp edge",J. Acoust. Soc. Am., vol. 136, No. 1, pp. 22-29 (2014).

Yokota et al., "A High-integrated Micromotor using Electro-conjugate Fluid (ECF)", Journal of Robotics and Mechatronics, vol. 17, No. 2, pp. 1-6 (2005).

English language abstract of JP2009136939 (2009).

ULTRASONIC ACTUATOR DEVICE AND APPLICATIONS THEREOF

BACKGROUND OF THE INVENTION

The invention relates to an ultrasonic actuator device, comprising in particular a movable actuator arm arrangement and at least one ultrasonic driver unit, which is arranged for driving the actuator arm arrangement by acoustic streaming. Furthermore, the invention relates to an operational instrument, e. g. a medical instrument, like an endoscope, a biomedical device for minimally invasive surgery, and/or a catheter, or a mechanical machine apparatus, comprising at least one ultrasonic actuator device. Furthermore, the invention relates to methods of using the ultrasonic actuator device. Applications of the invention are available e.g. in the fields of miniaturized actuators, micro actuators, wireless machines, measuring devices, and medical endoscope technology. Further applications include wireless control of tools and machinery.

For describing the background of the invention, particular reference is made to the following publications:
[1] Faulhaber: Brushless DC-Micromotor 0206, Data sheet (http://www.u-motor.com.cn/BL-motorF/PDF/0206.pdf);
[2] D. K.-C. Liu et al. in "Acoust. Sci. & Tech." 31:2, 115-23 (2010);
[3] U.S. Pat. No. 5,770,913;
[4] S. Yokota et al. in "Journal of Robotics and Mechatronics" 17:2, 142 (2005);
[5] A. H. Epstein. in "Proceedings of ASME Turbo Expo 2003" Atlanta, Ga., USA, Jun. 16-19, 2003;
[6] US 2013/0271088 A1;
[7] U.S. Pat. No. 6,272,922 B1;
[8] A. Denisov et al. in "Journal of Microelectromechanical systems" 23: 3, 750-9 {2014);
[9] U.S. Pat. No. 8,147,403 B2;
[10] A. Hashmi et al. in "Lab on a chip" 12: 4216-27 (2012);
[11] R. J. Dijkink et al. in "J. Micromech. Microeng." 16: 1653-9 (2006);
[12] J. Feng et al. in "MEMS 2013", Taipei, Taiwan, Jan. 20-24, 2013;
[13] J. Feng et al. in "MEMS 2014", San Francisco, Calif., USA, Jan. 26-30, 2014;
[14] U.S. Pat. No. 5,906,579 A;
[15] M. Ovchinnikov et al. in "J. Acoust. Soc. Am." 136: 1, 22-9 (2014); and
[16] N. Nama et al. in "Lab on a chip" 14:15, 2824-36 (2014).

The miniaturization of motors and machines that perform a mechanical task is extremely challenging, but important as could for instance enable minimally invasive biomedical devices for in vivo diagnostics and surgery. Currently, miniaturization of micro machinery is hindered by the size of the available actuators and the control and electronics that is needed to operate them. Electromagnetic motors, which work at larger scales (with diameters larger than about a centimeter), are difficult to miniaturize to below one millimeter. One of the smallest commercial electromagnetic motor is 1.9 mm in diameter and 6 mm in length [1].

In recent years, researchers therefore developed new miniaturized actuators, including electrostatic MEMS (Micro-electro-mechanical-system) motors, an electro-conjugate fluid motor, piezoelectric motors, pneumatic actuators, and a MEMS gas turbine engine [2-5]. The size of these actuators is much reduced compared with traditional actuators. However, a drawback common to all of these actuators is that they are all connected to complex wire connections or tubes to provide the power and to control the actuation. This problem limits the application of these actuators, and means that their overall size is also bigger. Multiple degrees-of-freedom are essential in positioning or steering miniaturized machines. Actuators for multiple degrees-of-freedom require an increasing number of wires (or tubes) as the degree-of-freedom increases, as besides the power additional control cables are needed, which dramatically increases the complexity and rigidity of the connections, and eventually causes operational problems if the device is too small. This means that the overall diameter of the device is at least several millimeters, whereas applications for endoscopes for instance require smaller diameter devices.

Ultrasound has been proposed to transfer power wirelessly [6-7]. However, these approaches convert mechanical vibration to electricity using the piezoelectric effect and then utilize the electricity to power a device. This electricity conversion process adds additional complexity and suffers from low efficiency.

Denisov et al. reported a mechanical system that is remotely excited by ultrasound and converts acoustic energy into motion using a receiving membrane coupled with a discrete oscillator [8]. In that case, the energy conversion relies on the resonance of the solid membrane, thus a large area and a restricted shape are required for the device. This disadvantage can be overcome through the conversion of ultrasonic energy directly to mechanical motion via acoustic streaming, as proposed in [9-13] and the present specification. Advantageously, mechanical motion by acoustic streaming does not require conversion to electric power.

It is well known that oscillating bubbles in fluids can cause acoustic streaming. Many microfluidic pumps and mixers are based on this phenomenon [10]. It was shown by Dijkink et al. that an oscillating bubble in a tube can be used as an ultrasonic actuator for turning a cantilever arm at centimeter scale [11]. Recently, a sub-millimeter scale "swimmer" in a microfluidic channel was propelled by the same mechanism as reported by Feng et al. [12-13]. However, these publications have been described for investigating the acoustic streaming mechanism only. The propelled components are not practically usable as actuators in terms of limited movability, e.g. on a circle [11], and limited usable driving force. Yet another approach uses a capsule device for in vivo sensing that is propelled by acoustic streaming [9]. However, the streaming is based on an on-board energy storage in the capsule, resulting in a limited miniaturization capability.

From an application point of view, current endoscopes with small overall diameter, as are for instance used in urology, only have one bending section near the tip of the endoscope with only one degree-of-freedom. Magnetic catheter steering was reported and used in clinics [14], but all the magnets are under the same magnetic field, thus it is unable to address individual actuators through magnetic approach. Thus, due to restrictions of actuator mechanisms, conventional medical instruments have restricted applicability.

Other mechanical machines, like current robot arms for operation in inaccessible environments, suffer from the large size and complicated structure of current actuators, thus have restricted applicability as well.

An objective of the invention is to provide an improved ultrasonic actuator device, which is capable of avoiding limitations and disadvantages of conventional techniques. Furthermore, methods of using the ultrasonic actuator device are to be provided. In particular, the objective of the invention to provide the ultrasonic actuator device having a simple structure, improved miniaturization capability, improved integration capability and/or reduced complexity of power supply and control. It is a further objective of the invention to provide an improved operational instrument, e.g. a medical instrument and/or a mechanical machine apparatus, which is capable of avoiding limitations and disadvantages of conventional techniques. In particular, the operational instrument is to be provided with extended functionality and applications.

The above objectives are solved by an ultrasonic actuator device, an operational instrument and a method comprising the features of the invention.

SUMMARY OF THE INVENTION

According to a first general aspect of the invention, the above objective is solved by an ultrasonic actuator device comprising an actuator arm arrangement and an ultrasonic driver device with at least one ultrasonic driver unit for driving the actuator arm arrangement.

The actuator arm arrangement (or: end effector) generally comprises at least one actuator arm (or: linkage) which is configured for coupling with a support structure and with a functional component to be moved relative to the support structure. A proximal end of the actuator arm arrangement is arranged for a connection with the support structure, while a distal end of the actuator arm arrangement is arranged for carrying or providing the functional component. The actuator arm arrangement includes a first actuator section (including the proximal end) for coupling with the support structure and a second actuator section (including the distal end) being movable relative to the first actuator section. The second actuator section can be movably coupled with the support structure as well. Due to the coupling with the support structure, the actuator arm arrangement is arranged for operation as a tethered actuator arm arrangement. In a single arm embodiment, the first and second actuator sections are portions of one single flexible actuator arm, and in a multiple arm embodiment, the first and second actuator sections are actuator arms being coupled with each other.

The at least one ultrasonic driver unit is arranged for creating an acoustic streaming in a fluid (liquid or gaseous) medium coupled with the actuator arm arrangement, e.g. surrounding the actuator arm arrangement. The ultrasonic driver unit has a driving surface, the driving surface or a part of it being capable of vibration at a driver frequency (preferably resonance frequency of the ultrasonic driver unit) and which is acoustically coupled with the medium. The acoustic streaming generates a driving force moving and/or setting the actuator arm arrangement in space. The at least one ultrasonic driver unit is coupled with at least one of the first and second actuator sections for driving the actuator arm arrangement. By operating the at least one ultrasonic driver unit, acoustic driving force(s) move the second actuator section and the first actuator section relative to each other.

According to the invention, the actuator arm arrangement is movable (or adjustable) with at least two degrees of freedom, including translational and/or rotational degrees of freedom. Moving the actuator arm arrangement includes at least one of bending, pivoting, rotating and translating actuator sections of the actuator arm arrangement. The second actuator section can be moved relative to the support structure by moving the actuator sections of the actuator arm arrangement independently along at least two independent different translation and/or rotation directions. The inventors have found that the tethered actuator arm arrangement with the at least two degrees of freedom driven with the at least one ultrasonic driver unit provides advantages in terms of both a simplified structure and control of the ultrasonic actuator device.

According to a second general aspect of the invention, the above objective is solved by an operational instrument comprising at least one ultrasonic actuator device of the above first aspect of the invention and at least one functional component which is coupled with or provided by the second actuator section of the actuator arm arrangement. Advantageously, the ultrasound-driven, multiple degrees of freedom actuator arm arrangement offers new applications and facilitated operations e.g. of a medical instrument, like an endoscope, a biomedical device for minimally invasive surgery or a catheter, or a robot arm and/or micro tool of a mechanical machine apparatus.

According to a third general aspect of the invention, the above objective is solved by a method of operating the ultrasonic actuator device of the above first aspect of the invention, wherein the ultrasonic driver device is controlled, such that the second actuator section is moved and/or adjusted in space relative to the first actuator section with at least two degrees of freedom.

Advantageously, the invention offers a plurality of options for providing the at least one ultrasonic driver unit, which can be selected in dependency on the particular use of the invention. According to a preferred embodiment of the invention, at least two ultrasonic driver units are provided which are coupled with at least one of the first and second actuator sections. Alternatively, one single ultrasonic driver unit is sufficient for driving one of the first and second actuators sections with one degree of freedom, whereas movements along the other degree of freedom preferably can be provided by an elastic reset force.

With the embodiment using two or more ultrasonic driver units, at least two ultrasonic driver units are coupled with the first actuator section or with the second actuator section, or at least one ultrasonic driver unit is coupled with each of the first and second actuator sections, resp. The ultrasonic driver units preferably have different driving directions. The driving surfaces of the ultrasonic driver units face to the different directions, resp. Advantageously, with this embodiment, the setting of the actuator arm arrangement can be obtained exclusively by acoustic streaming, thus simplifying the structure of the ultrasonic driver device.

Each of the at least two ultrasonic driver units can be used for driving the actuator arm arrangement with a specific degree of freedom. Alternatively, ultrasonic driver units can be operated in combination for driving the actuator arm arrangement with a specific degree of freedom, e.g. a rotational degree of freedom. Thus, with particularly preferred variants, the at least two ultrasonic driver units have non-opposite, in particular orthogonal, driving directions. Alternatively, the at least two ultrasonic driver units may have opposite driving directions.

According to a further preferred embodiment of the invention, the at least two ultrasonic driver units have different driver frequencies, in particular different resonance frequencies. Advantageously, this allows a selective operation of the ultrasonic driver units by a common control signal including one or multiple different control signal frequencies.

According to the multiple arm embodiment of the invention, the actuator arm arrangement comprises at least two actuator arms. A first actuator arm comprises the first actuator section, and a second actuator arm comprises the second actuator section, wherein the first and second actuator arms are coupled with each other. Each of the first and second actuator arms can be a flexible, bendable arm or a stiff arm. Preferably, the actuator arms are movably coupled with each other, e.g. via a ball joint, a pivot bearing, a flexible hinge or a hinge joint. According to a further alternative of the invention, the first and second actuator arms can be coupled via further actuator arms, which can be provided with at least one further ultrasonic driver unit.

According to a further modification of the invention, at least one of the first and second actuator sections is a preloaded actuator section, which is arranged to be movable against an elastic reset force. The preloaded actuator section preferably is used with the embodiment having one single ultrasonic driver unit, so that one of the degrees of freedom of the arm arrangement can be provided by moving the preloaded actuator section by the elastic reset force. Alternatively, the preloaded actuator section can be used with the embodiment having two or more ultrasonic driver units.

According to a first variant, the preloaded actuator section can be made of an elastically deformable material, so that the elastic reset force is created by the preloaded actuator section itself. According to a further variant, an elastic joint can be provided between the first and second actuator sections, so that the elastic reset force is created by the elastic joint. According to a further variant, at least one elastic component, like a spring can be connected with the preloaded actuator section.

According to a particularly preferred embodiment of the invention, both of the first and second actuator sections are preloaded actuator sections with different reset forces, which are movably coupled via a latching mechanism. One of the preloaded actuator sections is provided with the at least one ultrasonic driver unit driven against the reset force of the preloaded actuator section. In response to driving the ultrasonic driver unit, the latching mechanism can be released. The other one of the preloaded actuator sections is provided with a spring load driver unit coupled with the support structure. In response to releasing the latching mechanism, the preloaded actuator section is moved which is coupled with the spring load driver unit.

According to a preferred example, the spring load driver unit is a torsion spring having a torsion spring axis and carrying the associated preloaded actuator section, which is arranged for a rotation of the preloaded actuator section about the torsion spring axis. Advantageously, this allows that the preloaded actuator section driven by the torsion spring is rotated when the latching mechanism is released by the other preloaded actuator section driven by the ultrasonic driver unit. With an alternative embodiment, the spring load driver unit is e.g. a leaf spring.

According to further preferred embodiments of the invention, the at least one ultrasonic driver unit may comprise a passive ultrasonic driver unit or an active ultrasonic driver unit.

The passive ultrasonic driver unit has an array of oscillating elements (oscillating micro-structures), which can be either on the surface of the actuator sections or prepared on a surface to be attached to the actuator sections, like fluid cushions, in particular bubbles, and/or tips, having a resonance frequency and providing the driving surface. In response to an application of ultrasound with a frequency matching the resonance frequency, the oscillating elements vibrate for creating the acoustic streaming. Preferably, the array of oscillating elements comprises at least two oscillating elements, particularly preferred arranged as a row or a matrix of rows and columns. Fluid cushions (gas or liquid buffers, bubbles) can be provided at receptacle structures (cavities) of the surface of the ultrasonic driver unit, and they comprise e.g. gaseous bubbles for creating acoustic streaming in a liquid or gaseous cushions for creating acoustic streaming in a gas (in particular air stream). The gaseous cushions can be formed by gas captured in the cavities.

According to a first variant, the ultrasound is applied with an ultrasonic transducer (ultrasonic source) being arranged with a distance from the actuator arm arrangement. Contrary to conventional approaches having complex power and control wires, the use of the passive ultrasonic driver unit offers the advantage of a wireless operation of the ultrasonic driver unit. In particular contrary to [9], the ultrasonic source is separately placed at a distance from the actuator.

According to a second variant, the ultrasonic transducer for powering the passive ultrasonic driver unit is a component of the ultrasonic driver device. The ultrasonic transducer can be fixedly coupled with the ultrasonic actuator device, e.g. with the actuator arm arrangement.

The active ultrasonic driver unit comprises at least one oscillator transducer having a resonance frequency and providing the driving surface being acoustically coupled with the surrounding medium. In response to an application of a control voltage, the oscillating transducer vibrates for creating the acoustic streaming. The control voltage is supplied from a power source which is included in the ultrasonic actuator device. Accordingly, the active ultrasonic driver unit is wire-connected with the power source.

According to a particularly preferred embodiment of the invention, the ultrasonic driver device comprises at least two oscillator transducers having different resonance frequencies and being electrically connected in parallel with the power source. Advantageously, the parallel connection of the oscillator transducers allows the provision of only one wire connection (typically two lines) for powering and controlling all oscillator transducers simultaneously. Each of the oscillator transducers can be individually addressed by the resonance frequency thereof. Despite of the provision of only two lines, multiple degrees of freedom can be achieved. This is in contrast to conventional electric connections requiring at least one wire for each transducer plus a common ground wire. Advantageously, the parallel connection method of this embodiment enables the control of many transducers with only two wires in total, which minimize the effect of the wire to the movement of the ultrasonic actuator device.

According to a further preferred feature of the invention, the second actuator section carries at least one functional component. The functional component is connected with the movable portion of the actuator arm arrangement, e.g. at the distal end thereof or alternatively with a distance from the distal end. The functional component can provide the distal end of the actuator arm arrangement. The actuator arm arrangement and the ultrasonic driver device are arranged for at least one of moving and adjusting a position and/or an orientation of the functional component. The actuator arm arrangement can be provided with a stiffness being sufficient for stable holding and moving the at least one functional component at an application site, e.g. in a body liquid or in biological tissue. The inventors have found that the actuator arm arrangement with the additional mass of the functional component can be moved with the ultrasonic driver device. On the contrary, e.g. [11] only shows that an ultrasonic driver can propel itself.

The term "functional component" refers to any component which is capable of a physical (e.g. mechanical, electrical, magnetic, optic and/or thermal) and/or chemical interaction with the surrounding. Advantageously, there is a broad range of available functional components, preferably comprising at least one of a tool, a gripper, a pin, a needle, an electric contact, a sensor, a camera, a mirror, an optical fiber, a light source and a substance supply.

If the functional component comprises parts which are movable relative to each other, e.g. a tool, like a gripper, having movable tool sections, the ultrasonic driver device may include at least one further ultrasonic driver unit (or: ultrasonic tool driver unit) being arranged for driving the movable parts, e.g. for actuating the tool.

In summary, the following advantages and features can be obtained with the invention:

1. Acoustic streaming is used to shape and control a mechanically tethered actuator or end-effector, such as a robotic arm, or the end-effector of a medical instrument, like an endoscope;

2. The acoustic streaming can be driven by ultrasonic wave wirelessly and realized on a surface, which contains e.g. a two-dimensional array of micro-structures, e.g. an array of sharp tips, or an array of small cavities that can hold gas bubbles etc.;

3. The acoustic streaming can be realized on the surface of a vibrating ultrasonic transducer, which is excited by an electrical control signal through wire connection;

4. For either scheme without or with wire connection, the actuator arm arrangement has multiple degrees of freedom. Each degree of freedom is preferably orthogonal to each other and can be individually addressed by a unique ultrasonic resonance frequency. In the wireless setup, the ultrasound wave frequency corresponds to the resonance frequency of the micro-structures; in the wire-connected setup, multiple transducers are preferably connected in a parallel circuit to minimize the number of wires, but each has different resonant frequency according to different size or load; and 5. An actuator arm can be used as a latch to control the motion of a mechanically preloaded arm. The mechanically preloaded arm (typically preloaded with a spring) drives the movement (rotation or translation) of an end effector with a large force, and the ultrasonic streaming actuator arm serves as a latch, which controls the movement (move or stop) by the on or off state of the streaming.

BRIEF DESCRIPTION OF THE DRAWINGS

Further details and advantages of the invention are described in the following with reference to the attached drawings, which show in.

DETAILED DESCRIPTION OF PREFERRED EMBODIMENTS

In the following, exemplary reference is made to endoscope applications of an inventive ultrasonic actuator device. The endoscope for in vivo diagnostics is a possible application of the ultrasonic streaming wireless or wire-bound actuator of the invention. On the one hand, a medical device in vivo requires a small size and simple access to power; on the other hand, ultrasound is already used in many medical procedures, including imaging, the break-up of (kidney) stones, tissue ablation etc. Ultrasound has been shown to penetrate the human body and to be safe if the exposed power is appropriately controlled. It is emphasized that the invention is not restricted to the endoscopy example, but rather can be used also e.g. with other medical devices, like a biomedical device for minimally invasive surgery and/or a catheter, or with measuring devices or robot arms of mechanical machines, e.g. a robot arm for use in water, e.g. outside a submarine vehicle.

Embodiments of the inventive ultrasonic actuator device are described in particular with reference to the structure of the actuator arm arrangement and the ultrasonic driver units. Details of generating ultrasound and/or control signals driving ultrasonic transducers can be implemented as it is known from conventional ultrasound techniques.

Figure 1:
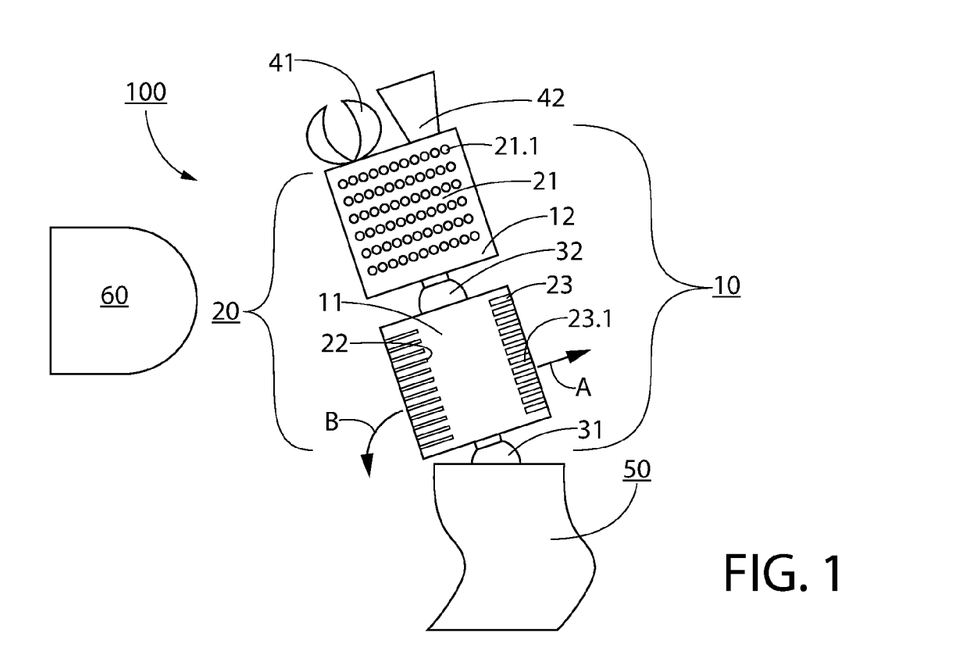
FIGS. 1 and 2: schematic representations of preferred embodiments of an ultrasonic actuator device according to the invention.
Figure 2:
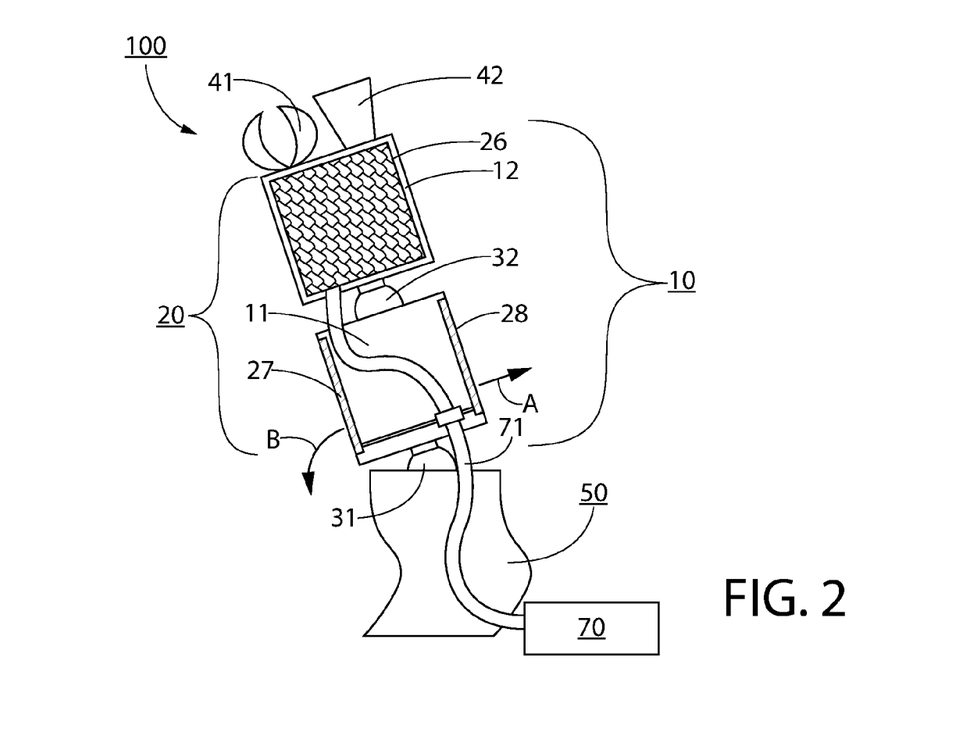

FIGS. 1 and 2 show embodiments of an ultrasonic actuator device 100 comprising an actuator arm arrangement 10 and an ultrasonic driver device 20 including passive ultrasonic driver units 21, 22, 23 (FIG. 1) or active ultrasonic driver units 26, 27, 28 (FIG. 2). With both embodiments, the actuator arm arrangement 10 includes a first actuator arm 11 and a second actuator arm 12. The ultrasonic actuator device 100 is arranged in a surrounding medium, like a liquid, e.g. water, or a gas, e.g. air (see FIG. 4).

The first actuator arm 11 provides a first actuator section coupled via a first ball joint 31 with a support structure 50, which is a part, e.g. a shaft or another movable arm, of an endoscope (not shown). The second actuator arm 12 is coupled via a second ball joint 32 with the first actuator arm 11. By the provision of to the first and second ball joints 31, 32, each of the first and second actuator arms 11, 12 has three degrees of freedom.

The second actuator arm 12 provides a second actuator section to which functional components, including a gripper 41 and a camera 42 are attached. The gripper 41 and the camera 42 are structured and controlled via cable connections (not shown) as it is known from conventional endoscopes. The gripper 41 can be driven with an ultrasonic tool driver unit (not shown) for creating acoustic streaming, wherein the ultrasonic tool driver unit is structures like an ultrasonic driver unit of the inventive ultrasonic actuator device 100.

The first and second actuator arms 11, 12 each comprise a cuboid (square bar) with side surfaces facing to different directions and carrying the ultrasonic driver units 21, 22, 23, 26, 27, 28. According to FIG. 1, the ultrasonic driver units 21, 22, 23 comprise arrays of receptacles each including a gas bubble (e.g. 21.1). The receptacles have a cylindrical shape. The gas can be air, which is trapped in the receptacles when immersed into the water or generated by cavitation effect under ultrasonic pressure. It can also be another gas, e.g. SF6, which is preferably insoluble in water.

The arrays of receptacles can be formed (e.g. etched or engraved) in the surface of the actuator arm material. Alternatively, the arrays of receptacles can be formed in a thin layer applied to the surfaces of the actuator arms. As an example, a soft tape can be used which has cavities on one side, and it can be easily pasted on a solid surface to provide the ultrasonic driver unit.

At least two, preferably all four sides of the first and second actuator arms 11, 12 are covered with receptacles receiving gas bubbles, which have different sizes on different sides of the first and second actuator arms 11, 12 (only three bubble arrays of the ultrasonic driver units 21, 22, 23 are shown as example in FIG. 1). For instance, the ultrasonic driver units 22, 23 on opposite sides of the second actuator arm 12 are shown with receptacles having different dimensions and/or depths, thus accommodating bubbles with different sizes and resonance frequencies. Further examples of gas bubble arrays are shown in FIG. 3.

In response to an irradiation of the gas bubbles of the ultrasonic driver units 21, 22, 23 with ultrasound, the gas bubbles oscillate. Thus, acoustic streaming is created as indicated e.g. with arrow A representing water streaming perpendicular to a side of the first actuator arm 11. Furthermore, arrow B exemplifies acoustic streaming causing a rotation of the first actuator arm 11.

The ultrasound is created with an ultrasonic transducer 60 arranged with a distance from the ultrasonic actuator device 100. The excitation can be focused or not focused. If the ultrasonic actuator device 100 is provided as a part of an endoscope in a human body (not shown), the ultrasonic transducer 60 can be arranged outside of the body. With a preferred example, the ultrasonic transducer 60 is an ultrasound source head as used in conventional ultrasound imaging. Preferably, the ultrasonic transducer 60 is movable for an adjustment relative to the position of the ultrasonic actuator device 100. Alternatively, the ultrasonic transducer 60 is arranged inside the body to reduce the distance to the ultrasonic actuator device 100. Preferably, a miniaturized piezoelectric ultrasonic transducer 60 can be used, which e.g. can be inserted through the bore of the endoscope. With another alternative, the ultrasonic transducer 60 can be coupled with the support structure. The ultrasonic transducer 60 can be arranged for emitting ultrasound having different ultrasound frequencies, which are created simultaneously or in a time-sharing manner.

The dimensions of the first and second actuator arms 11, 12, the number of bubbles per array, the sizes of the bubbles and the ultrasound frequencies can be selected in dependency on particular application conditions of the ultrasonic actuator device 100. With a practical example, the actuator arm arrangement 10 has a longitudinal length of 8 mm, whereas the bubbles have diameters of e.g. 50 µm and ultrasound frequencies in a range of 20 kHz to 1 MHz is used.

Advantageously, the embodiment of FIG. 1 does not require a wire connection of the ultrasonic driver units 21, 22, 23 to be powered, so increasing the number of ultrasonic driver units or arms will not increase the complexity or rigidity of the endoscope. Therefore, it is possible to individually control many different actuator arms at the same time whilst ensuring a small design as possible with this embodiment.

In operation of the ultrasonic actuator device 100, at a certain ultrasound frequency, fluidic streaming of arrow A only happens on one side (in this case gas bubbles 23.1 are activated) and the first actuator arm 11 is rotated by the propulsion of that surface, and its rotating angle is controlled by the strength of the ultrasonic field. Ultrasound at different frequencies can be used in a time-shared manner, because the responsive time of the actuator arms 11, 12 in fluid (the time for it to recover to straight position) is much longer than one period of the ultrasound. Thus multiple frequencies can be executed in a time-shared manner, and the arms can keep their positions at a certain spatial angle (as shown in FIG. 1). With the first and second actuator arms 11, 12 working like this, the position and/or orientation of the end tip of the endoscope can be set and controlled e.g. in three spatial dimensions and additionally in one temporal dimension.

According to FIG. 2, the ultrasonic driver units 26, 27, 28 comprise oscillator transducers each including e.g. a piezoelectric crystal or a polymer transducer. The oscillator transducers are connected in parallel via a wire connection 71 with a controllable power source 70. In response to control signals from the power source 70 the oscillator transducers of the ultrasonic driver units 26, 27, 28 can be activated. The oscillator transducers on different sides of the first and second actuator arms 11, 12 have different resonance frequencies. Movements of the first and second actuator arms 11, 12 can be driven, e.g. along the arrows A and B as mentioned above, by applying specific control signals with selected amplitudes and frequencies to the oscillator transducers.

Figure 3A:
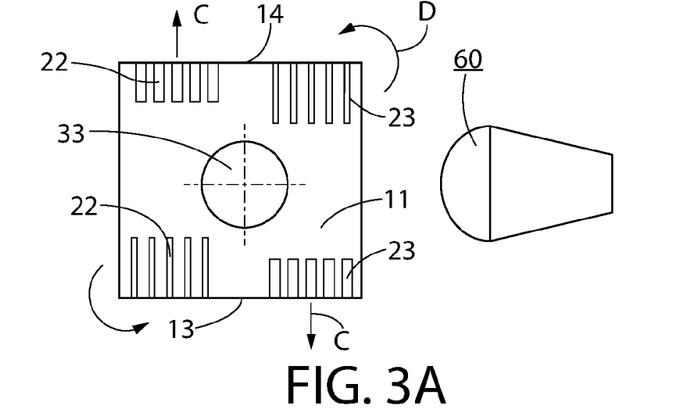
FIGS. 3 to 5: schematic representations of arrays of oscillating elements used in an ultrasonic actuator device according to the invention.
Figure 3B:
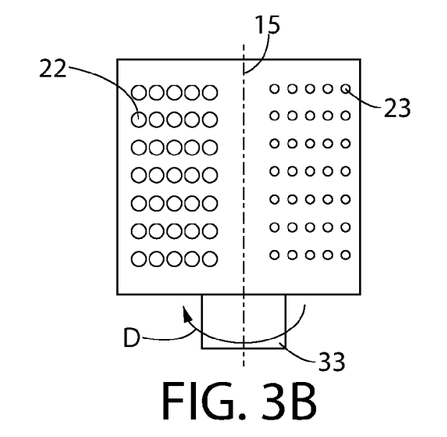

FIG. 3 shows a variant of an actuator arm 11 having two ultrasonic driver units 22, 23 on each of two opposite sides 13, 14 thereof. FIG. 3A illustrates a cross-sectional view, while FIG. 3B is a side view of the actuator arm 11. A shaft 33 is provided for rotatably coupling with a support structure or another actuator arm (not shown). The actuator arm 11 is rotatable around a rotation axis 15 defined by the longitudinal direction of the shaft 33.

The ultrasonic wave from the ultrasonic transducer 60 propagates through the medium or body (e.g. water) and excites the oscillation of the gas bubbles that are resonant at this frequency, thus the streaming of water happens at the gas-water interface and the direction of the streaming flow is perpendicular to and away from the surface, as indicated by the straight arrows C in FIG. 1. The ultrasonic driver units 22, 23 are arranged on the sides 13, 14 such that a torque can be generated and a rotation (arrow D) can be obtained by selectively vibrating the bubbles of the ultrasonic driver units 22 having receptacles with larger diameters or the ultrasonic driver units 23 having receptacles with smaller diameters.

The size and shape of the gas bubbles is mainly determined by the size and shape of the receptacles, thus they can be excited by a unique (and different) ultrasound frequency. In this embodiment, the gas bubbles have different diameters and depth on the two opposite sides of the shaft of the actuator arm 11, thus counter-clockwise and clockwise rotations about the shaft can be realized at two different frequencies.

Figure 4:
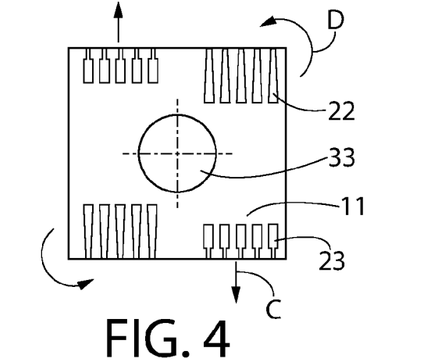

With an alternative embodiment, as shown in FIG. 4, a gas, like air can be used as the surrounding propagation medium for ultrasound, although its acoustic resistance is higher than liquid. Accordingly, an actuator arm 11 of an actuator arm arrangement can be placed in air, and the streaming of air is caused by the resonance of air cushions in the receptacles of the ultrasonic driver units 22, 23 on the sides of the actuator arm 11. The dimensions and/or shapes of the receptacles can be designed to achieve efficient acoustic resonance at different frequencies. Acoustic streaming can be obtained, see e.g. arrow C, for obtaining a rotation (arrow D) around the axis of shaft 33. Preferably, the receptacles have a shape with a diameter decreasing toward the opening side surface of the actuator arm, e.g. a step-like shape or a conical shape, thus improving a holding of vibrating air cushions in the receptacles.

Figure 5:
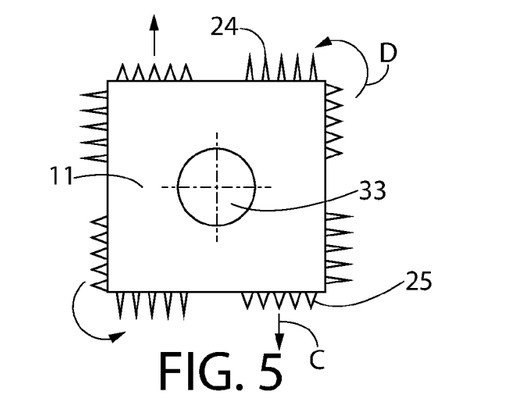

The rotating actuator arm 11 of FIGS. 3 to 5 provides an oscillating element array streaming motor operated in a fluid medium, which represents an independent subject of the invention. As mentioned above, the arrays of receptacles can be formed in the surface of or as a separate layer on the actuator arm material. Furthermore, the actuator arm can provide a functional component, which carries the array of oscillating elements.

FIG. 5 shows a further embodiment of the invention, wherein solid tips are utilized as oscillating elements of passive ultrasonic driver unit 24, 25. Four side surfaces of the actuator arm 11 can be all covered with sharp edges, but of different sizes on two halves split by the middle axis of shaft 33. As reported in literature [15-16], tips can also result in streaming under ultrasonic excitation. The sharp tips are made of e.g. silicon with a diameter of 100 µm at larger end and 10 µm at sharper end and a height of 200 µm. Although the streaming strength caused by the sharp tips is not as large as that caused by the bubbles, the advantage of this embodiment over the embodiments of FIGS. 3 and 4 is that the solid tips are more stable than the bubbles or air cushions.

Figure 6:
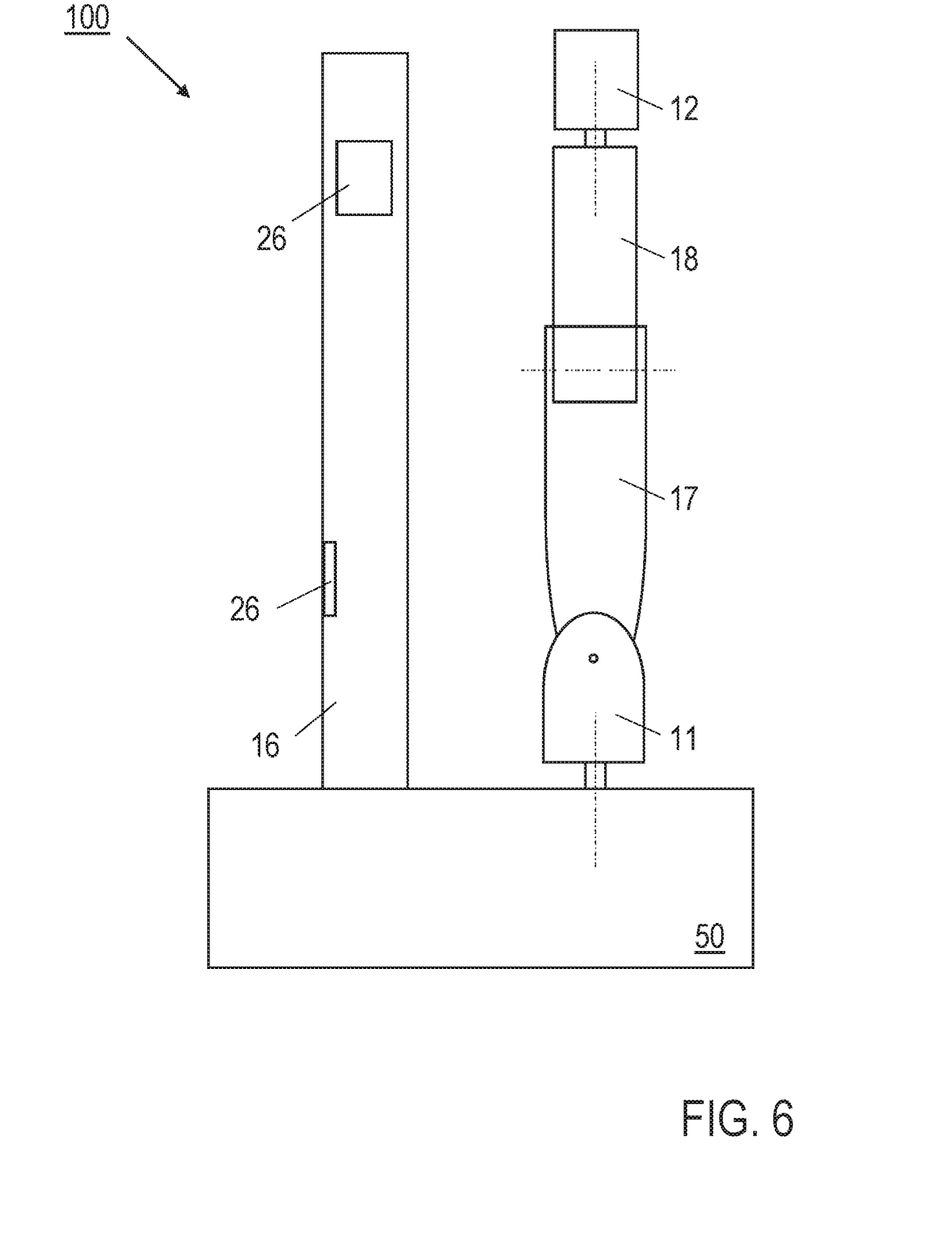
FIG. 6: a schematic representation of a further preferred embodiment of an ultrasonic actuator device according to the invention.

The actuator arm arrangement 10 is shown with two actuator arms 11, 12 in FIGS. 1 and 2. Alternatively, only one actuator arm 16 or more than two actuator arms 11, 12, 17 and 18 can be provided as schematically shown in FIG. 6. The single actuator arm 16 is made of a flexible material, e.g. PDMS (poly(dimethylsiloxane)), carrying active or passive ultrasonic driver units 26 as described above. The actuator arm 16 preferably is elastically deformable, thus providing a preloaded actuator section.

The ultrasonic driver units 26 are arranged such that the driving surfaces thereof face towards different directions in space. By activation with ultrasound or control signals, the ultrasonic driver units 26 can be specifically driven, so that the single actuator arm 16 is deformed in space. Furthermore, the actuator arms 11, 12, 17 and 18 can be provided for obtaining further degrees of freedom for manipulating the second actuator arm 12 relative to the support structure 50.

Figure 7:
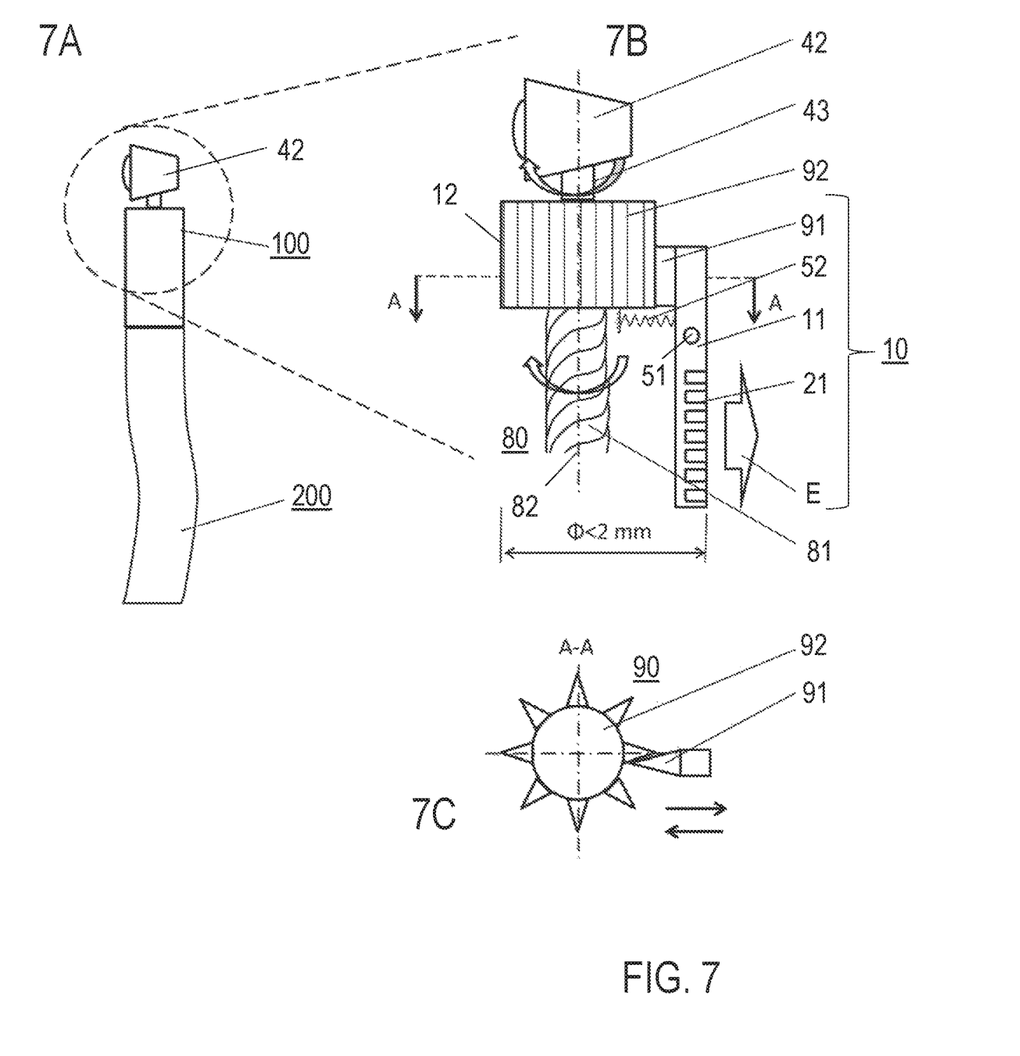
FIGS. 7 and 8: schematic representations of preferred embodiments of an ultrasonic actuator device according to the invention, provided with actuator sections being coupled via a latching mechanism.

FIG. 7 illustrates an embodiment of the invention, wherein the ultrasonic actuator device 100 is provided with one single ultrasonic driver unit 21 and a spring load driver unit 80. FIG. 7A schematically illustrates an endoscope 200 being provided with the ultrasonic actuator device 100, which carries a camera 42. The camera 42 is to be rotated on request relative to the longitudinal axis of the endoscope 200.

The main purpose of this embodiment is to remote control the orientation of the camera 42 on the tip of the endoscope 200. In some working environments in the human body, it may need larger forces (in the range of 1-1000 mN) to move the end effector to overcome the fluidic flow or resistance of soft tissues. Similarly, larger forces are necessary for microsurgical applications. The direct drive of the ultrasonic streaming actuator, when dimensioned at several millimeters, may not provide enough force for these applications, and complicated mechanical transmission mechanisms to amplify the force (e.g. a gear box) are difficult to implement at the millimeter and sub-millimeter length-scale. Therefore, the ultrasonic driver unit 21 can be coupled with the spring load driver unit 80 providing a second wireless actuator. The ultrasonic driver unit 21 is then not used to drive the movement of the camera head, but to actuate a control mechanism that is used to control the secondary actuator. For instance, the ultrasonic driver unit 21 can be used to move a switch or a latch which in turn controls the second wireless actuator, such as a mechanically preloaded spring, which can provide the necessary force for the application, as illustrated with further details in FIG. 7B.

According to FIG. 7B, the ultrasonic actuator device 100 comprises an actuator arm arrangement 10 comprising a first actuator arm 11 and a second actuator arm 12. The first actuator arm 11 is a stiff lever, which is coupled via a pivot 51 with the support structure of the endoscope 200 (not shown in FIG. 7B). At an upper end, the first actuator arm 11 has a jaw 91 in engagement with a ratchet 92 of the second actuator arm 12. The upper end with the jaw 91 is preloaded against the support structure with an elastic component, like the tension spring 52. A lower portion of the first actuator arm 11 carries the ultrasonic driver unit 21, like a bubble array.

The second actuator arm 12 has a cylindrical shape with the ratchet 92 on a circumferential surface thereof. The camera is coupled via a shaft 43 with the second actuator arm 12. The second actuator arm 12 is carried by a spring load driver unit 80 comprising a torsion spring 81, like a twisted elastic bar or wire, which is connected with the support structure. The torsion spring 81 defines a torsion spring axis 82. The second actuator arm 12 can be continuously rotated around the torsion spring axis 82 if the ratchet 92 is released.

As illustrated in FIG. 7B, the camera 42 is carried by the second actuator arm 12 and connected to the preloaded twisted wire. The wire is very thin but can be as long as several centimeter, thus can be preloaded, i.e. pre-twisted to several full rotations before applying the endoscope 200. For instance, one can envision loading the twisted wire from the outside before employing the endoscope 200. The wire may be polymeric. It serves as the torsion spring 81 and the release can be controlled with the ultrasonic driver unit 21 in vivo.

As schematically presented in FIG. 7C, jaw 91 and ratchet 92 provide a latching mechanism 90, which is actuated by the ultrasonic driver unit 21. Without an actuation of the ultrasonic driver unit 21, the jaw 91 blocks the ratchet 92 by the effect of the tension spring 52. In response to an actuation of the ultrasonic driver unit 21 by applying an external ultrasound source, the acoustic streaming is generated along arrow E. The first actuator arm 11 is moved against the elastic reset force of the tension spring 52, and the ratchet 92 is released, thus allowing the rotation of the camera 42. When the camera 42 reaches the right orientation, the ultrasound is turned off, liquid streaming stops and the first actuator arm 11 is pulled by the tension spring 52 to its original position, thus the jaw 91 stops the rotation of the ratchet 92 and camera 42. Other mechanical devices, e.g. escapement mechanism, can similarly be controlled by this mechanism, and realize stepped-wise motion of the preloaded arm 12.

Because the axis of pivot 51 of the first actuator arm 11 is perpendicular to the rotation axis 82 of the torsion spring 81, it does not require a large force to block the rotation, and only needs to overcome the friction between the jaw and the ratchet. Preloaded torsion springs are used in mechanical devices. The spring can for instance be about 100 µm in diameter and 10 mm in length. As an example, a preloaded twisted wire that has been pre-twisted 50 times may provide approximately 1 to 3 N·mm torque, which at a distance of 1 mm yields forces that exceeds the force of the direct ultrasonic actuator.

The embodiment of FIG. 7 illustrates the rotation of the camera 42 by the preloaded torsion spring 81 as an example only. Other functional components can be moved with the second actuator arm 12 as well (see below, FIG. 8). In summary, the embodiment of FIG. 7 combines the advantages of large driving force and wireless control of movement by ultrasound. The overall end effector can have a diameter that is smaller than 2 mm, and a length of a few millimeter to 10 mm, and it does not require any wire connection powering the actuator from outside, thus allows free movement of the endoscope and therefore permits the overall outside diameter of the endoscope to be smaller than what is currently possible. In addition all the functionality that one encounters with modern medical endoscopes (e.g. optical fibers, diagnostic, and fluidic tubes, as well as wires and grippers etc.) can be incorporated with the present invention.

Figure 8:
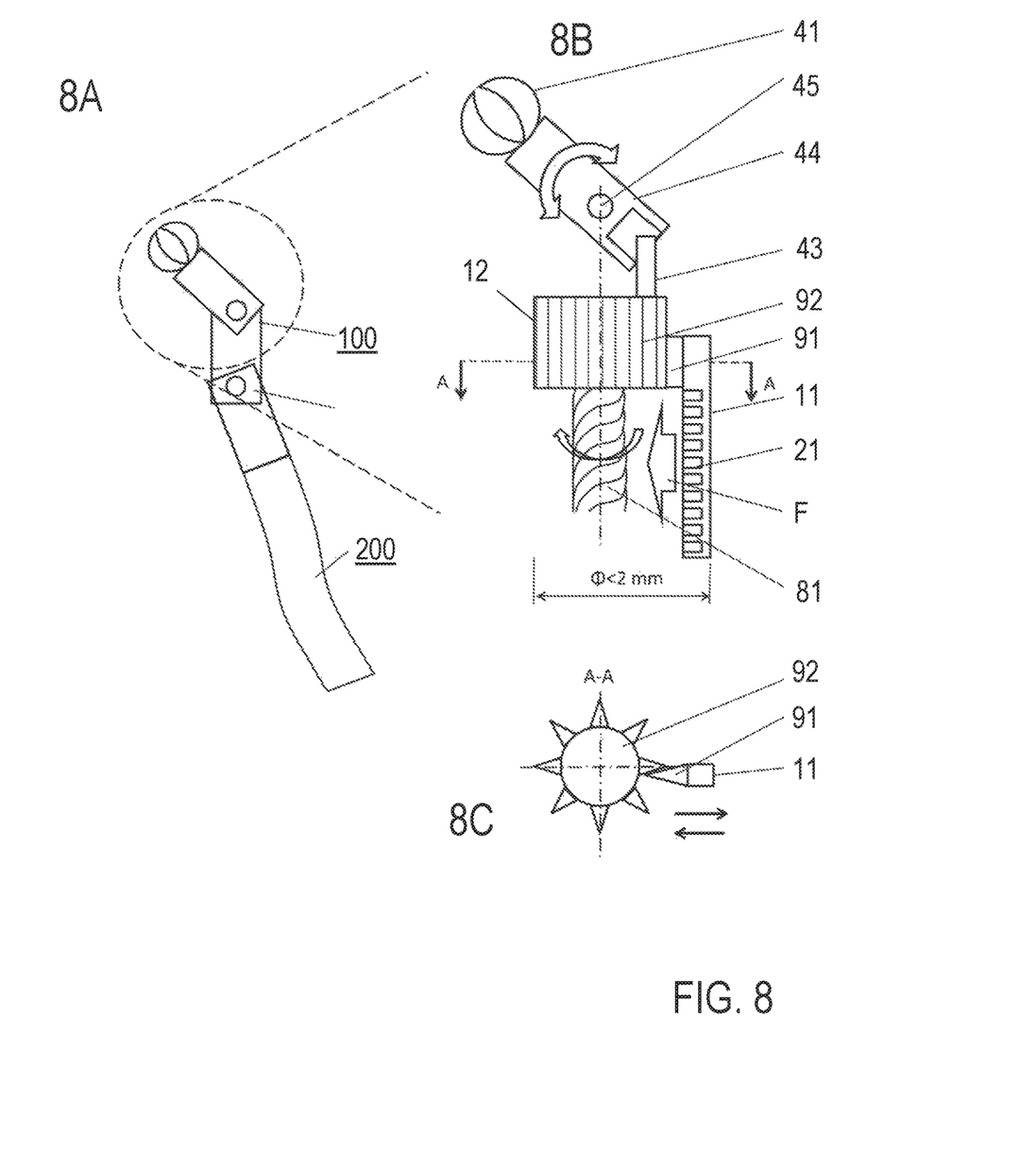

FIG. 8 illustrates features of further embodiments of an ultrasonic actuator device 100. FIG. 8A schematically shows an endoscope 200 provided with the actuator device 100. According to a first variant, the actuator device 100 can comprise two actuator arms 11, 13, which are mounted in series at the tip of the endoscope 200 and which have parallel axes or orthogonal axes depending on the application. The actuator arms 11, 13 can be structured as described above with reference to FIG. 1, 2 or 9. In particular, the two actuator arms 11, 13 have the same general structure, but differ in the resonance frequency of the ultrasound actuators.

According to a second variant, the actuator device 100 has two actuator arms 11, 12 and a latching mechanism 90 as shown in FIG. 8B. In this embodiment, the actuator device 100 can control the movement of a multiple degrees-of-freedom functional component, provided by a crank 43 and gripper 41. Furthermore, the form (continuous rotation, oscillation or translation) and the direction of the motion of the end effector can be converted from the driving motion of a preloaded spring.

According to FIG. 8B, the ultrasonic actuator device 100 comprises the first actuator arm 11 and the second actuator arm 12, which are coupled via the latching mechanism 90. The first actuator arm 11 is made of an elastically deformable material, like e.g. PDMS, which is coupled to a support structure (not shown) of the endoscope 200. The elastically deformable material creates an elastic reset force urging a jaw 91 at an upper end of the first actuator arm 11 to a ratchet 92 on a circumferential surface of the second arm 12. The ultrasonic driver unit 21, comprising e.g. an array of bubbles, is arranged on a side surface for the first actuator arm 11 such that in response to an application of ultrasound and the creation of acoustic streaming (arrow F), the jaw 91 is separated from the ratchet 92. The second actuator arm 12 has a structure with the ratchet 92 and the spring load driver unit 80 as described above with reference to FIG. 7B.

Similar to FIG. 7B, the torsion spring 81 is a pre-twisted wire, but the difference is that its continuous rotation is converted to an oscillation of the arm 44 carrying the gripper 41 around a perpendicular shaft 45 by an 'oblique crank and rocker' mechanism. When the crank 43 rotates continuously in one direction, the arm 44 oscillates around its own shaft 45 in both directions. This motion is suitable to control the shape and orientation of the endoscope tip and can also be easily integrated in series to realize multiple degrees-of-freedom linkages.

The oscillatory movement is controlled by the ultrasonic driver unit 21. However, in this embodiment, instead of the lever mechanism, the first actuator arm 11 is realized with the ultrasonic driver unit 21 as a linear segment with cavities on one side. When ultrasound of the corresponding frequency is applied from a suitable transducer (not shown), the streaming causes the first actuator arm 11 to bend and this in turn releases the ratchet 92, which allows the movement. Without ultrasound or with ultrasound at a frequency that is not resonant, the first actuator arm 11 returns to its original position and the jaw 91 locks the movement.

Multiple ultrasonic actuator devices can be provided with different resonance frequencies, thus the movement of each actuator arm arrangement can be independently and wirelessly controlled by an ultrasound source with adjustable frequency.

Figure 9:
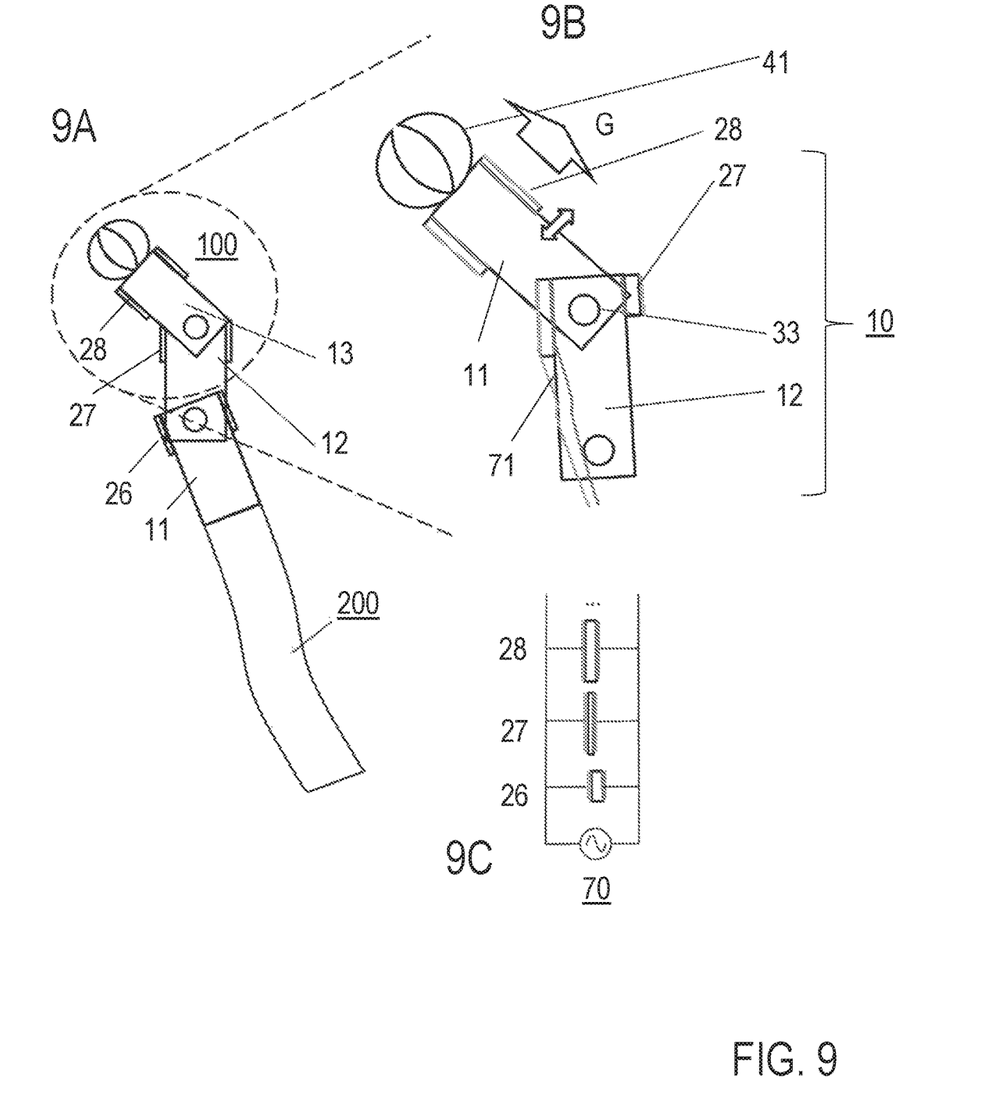
FIG. 9: a schematic representation of a further preferred embodiment of an ultrasonic actuator device according to the invention, provided with oscillator transducers.

FIG. 9 shows an embodiment of the invention, wherein the actuator arm arrangement 10 has three actuator arms 11, 12, 13 and the ultrasonic driver device 20 has multiple active ultrasonic driver units 26, 27, 28. The three actuator arms 11, 12, 13 are mounted in series at the tip of the endoscope 200 (FIG. 9A), and they have parallel axes or orthogonal axes (e.g. at 33) depending on the application. The distal actuator arm 13 carries a gripper 41 to be moved and adjusted with multiple degrees of freedom with the ultrasonic actuator device 100.

Each of the ultrasonic driver units 26, 27, 28 comprises ultrasonic transducers, in particular flat piezoelectric ceramic plates, which are connected via wires 71 with a controllable power source 70 (FIG. 9C). Acoustic streaming directly from the piezoelectric ceramic plates is used to drive the actuator arms 11, 12, 13 of the endoscope 200. The vibration along the thickness direction of the piezoelectric ceramic plates results in streaming in parallel to the vibrational direction (indicated by the arrow G in FIG. 9B). The piezoelectric ceramic plates are of different sizes (area and/or thickness) or different loads (mass attached on the vibrating surface), thus each has individual resonant frequency.

The piezoelectric ceramic plates are connected in parallel electrically (two electrodes are connected respectively to two wires 71) as shown in FIG. 9C. Thus, only two wires are needed to power multiple transducers to achieve multiple degrees-of-freedom, and the frequency of the driving signal can be chosen to address individual transducer. Although they are connected in parallel circuit electrically, the frequency of the driving control signal can be selected to match individual transducer's resonance frequency, thus control several degrees-of-freedom separately.

The advantage of the embodiment of FIG. 9 is that the power transmission is through wire connections 71, thus it has higher efficiency, much less attenuation and noise problem comparing with the transmission of ultrasonic wave through body tissues. It may also provide much more power to the ultrasonic driver units thus generates larger force than the wireless approach, because the power limit through wire is much higher.

The features of the invention disclosed in the above description, the drawings and the claims can be of importance individually or in combination or in sub-combination for the realization of the invention in its different embodiments.

What is claimed is:

1. An ultrasonic actuator device, comprising:
   an actuator arm arrangement including a first actuator section and a second actuator section, wherein the first actuator section is arranged for coupling with a support structure and the second actuator section is movable relative to the first actuator section, and
   an ultrasonic driver device including at least one ultrasonic driver unit being coupled with at least one of the first and second actuator sections for driving the actuator arm arrangement and for providing a movement of the second actuator section relative to the first actuator section, wherein
   the actuator arm arrangement is movable with at least two degrees of freedom, and
   the at least one ultrasonic driver unit comprises an array of oscillating elements being arranged for creating an acoustic stream in an adjacent medium in response to an application of ultrasound to the oscillating elements.

2. The ultrasonic actuator device according to claim 1, wherein
at least one of the first and second actuator sections is provided with at least two ultrasonic driver units having different driving directions.

3. The ultrasonic actuator device according to claim 2, wherein
the at least two ultrasonic driver units have non-opposite driving directions, or
the at least two ultrasonic driver units have opposite driving directions.

4. The ultrasonic actuator device according to claim 2, wherein
the at least two ultrasonic driver units have different resonance frequencies.

5. The ultrasonic actuator device according to claim 1, comprising
a first actuator arm providing the first actuator section, and
a second actuator arm providing the second actuator section, wherein
the first and second actuator arms are coupled with each other.

6. The ultrasonic actuator device according to claim 1, wherein
at least one of the first and second actuator sections is a preloaded actuator section, which is arranged to be movable against an elastic reset force, which is created by at least one of the preloaded actuator section itself, an elastic joint between the first and second actuator sections and at least one elastic component connected with at least one of the first and second actuator sections.

7. The ultrasonic actuator device according to claim 6, wherein
both of the first and second actuator sections are preloaded actuator sections, which are movably coupled via a latching mechanism, wherein
one of the first and second actuator sections is provided with the at least one ultrasonic driver unit, and
the other one of the first and second actuator sections is provided with a spring load driver unit.

8. The ultrasonic actuator device according to claim 7, wherein
the spring load driver unit comprises a torsion spring having a torsion spring axis and carrying the associated preloaded actuator section, which is arranged for a rotation about the torsion spring axis.

9. The ultrasonic actuator device according to claim 1, wherein
the at least one ultrasonic driver unit comprises an array of at least one of fluid cushions and tips, being arranged for creating the acoustic stream in the adjacent medium in response to the application of ultrasound provided by an ultrasonic transducer.

10. The ultrasonic actuator device according to claim 1, wherein
the ultrasonic driver device further comprises a power source arranged for creating a control voltage, and the at least one ultrasonic driver unit further comprises at least one oscillator transducer being connected with the power source and being arranged for creating an acoustic stream in an adjacent medium in response to an application of the control voltage provided by the power source.

11. The ultrasonic actuator device according to claim 10, wherein
the ultrasonic driver device comprises a plurality of oscillator transducers being connected in parallel with the power source.

12. The ultrasonic actuator device according to claim 1, wherein
the second actuator section carries or provides at least one functional component, and
the actuator arm arrangement and the ultrasonic driver device are arranged for at least one of moving and adjusting a position of the at least one functional component.

13. The ultrasonic actuator device according to claim 12, wherein
the at least one functional component comprises at least one of a tool, a gripper, a pin, a needle, an electric contact, a sensor, a substance supply, a camera, an optical fiber and a light source.

14. The ultrasonic actuator device according to claim 13, wherein
the at least one functional component comprises the tool, having movable tool sections, and
the ultrasonic driver device includes at least one ultrasonic tool driver unit being arranged for actuating the tool.

15. An operational instrument, comprising
a support structure, and
at least one ultrasonic actuator device according to claim 1, wherein
at least one functional component is coupled with the second actuator section of the actuator arm arrangement.

16. The operational instrument according to claim 15, wherein
said at least one functional component comprises at least one of a tool, a gripper, a pin, a needle, an electric contact, a sensor, a substance supply, a camera, a mirror, an optical fiber and a light source.

17. The operational instrument according to claim 15, wherein
the support structure is a medical instrument.

18. The operational instrument according to claim 17, wherein
the medical instrument is an endoscope device, a catheter or a biomedical device for minimally invasive surgery, or a mechanical machine apparatus.

19. A method of using an ultrasonic actuator device according to claim 1, comprising the step of
controlling the ultrasonic driver device, so that the second actuator section is moved or adjusted in space relative to the first actuator section, wherein
the actuator arm arrangement is moved with at least two degrees of freedom.

* * * * *